(12) United States Patent
Kim

(10) Patent No.: US 7,596,257 B2
(45) Date of Patent: Sep. 29, 2009

(54) MEDICAL IMAGE PROCESSING DEVICE METHOD AND PROGRAM FOR DISPLAYING A SECTION FOR A CLINICAL APPLICATION

(75) Inventor: Han-Joon Kim, Kobe (JP)

(73) Assignee: Imagnosis Inc., Hyogo (JP)

( * ) Notice: Subject to any disclaimer, the term of this patent is extended or adjusted under 35 U.S.C. 154(b) by 882 days.

(21) Appl. No.: 10/493,969

(22) PCT Filed: Oct. 31, 2002

(86) PCT No.: PCT/JP02/11336

§ 371 (c)(1),
(2), (4) Date: Apr. 29, 2004

(87) PCT Pub. No.: WO03/037189

PCT Pub. Date: May 8, 2003

(65) Prior Publication Data

US 2005/0018886 A1    Jan. 27, 2005

(30) Foreign Application Priority Data

Oct. 31, 2001    (JP)    ............................. 2001-335080

(51) Int. Cl.
*G06K 9/00*    (2006.01)
*G06T 15/20*    (2006.01)
*G09G 5/00*    (2006.01)

(52) U.S. Cl. ....................... 382/131; 382/154; 345/427; 345/650; 345/676

(58) Field of Classification Search ................. 382/131, 382/132, 154; 345/648, 649, 653, 419, 420, 345/421, 619, 620, 650, 652, 654
See application file for complete search history.

(56) References Cited

U.S. PATENT DOCUMENTS

| | | | | |
|---|---|---|---|---|
| 4,593,355 A | * | 6/1986 | Chase | ........................ 382/131 |
| 4,984,157 A | * | 1/1991 | Cline et al. | .................. 345/424 |
| 5,038,285 A | * | 8/1991 | Jouandet | ..................... 382/131 |
| 5,734,384 A | * | 3/1998 | Yanof et al. | .................. 345/424 |
| 6,065,475 A | * | 5/2000 | Qian et al. | ................... 600/436 |
| 6,484,048 B1 | * | 11/2002 | Hoshino et al. | ............. 600/410 |
| 6,603,868 B1 | * | 8/2003 | Ludwig et al. | ............... 382/128 |

(Continued)

FOREIGN PATENT DOCUMENTS

JP    1-134580    5/1989

(Continued)

*Primary Examiner*—Brian P Werner
*Assistant Examiner*—Anthony Mackowey
(74) *Attorney, Agent, or Firm*—Rabin & Berdo, P.C.

(57) ABSTRACT

A conventional medical image processing apparatus is capable of forming a section perpendicular to a reference plane, but has a drawback that a section intersecting the reference plane at a desired angle other than the right angle cannot be formed. A sectional line is defined in a three-dimensional image viewed perpendicularly to a reference plane. Then, the displayed image is switched to an image viewed along the sectional line, and a line indicative of the reference plane and a line indicative of a sectional plane based on the sectional line are displayed in the image. In turn, the line indicative of the displayed sectional plane is inclined with respect to the line indicative of the reference plane. Then, a sectional image taken along the sectional plane defined by the inclined line is displayed.

6 Claims, 9 Drawing Sheets

U.S. PATENT DOCUMENTS

| | | | |
|---|---|---|---|
| 6,807,292 B1 * | 10/2004 | Goto et al. | 382/128 |
| 6,898,302 B1 * | 5/2005 | Brummer | 382/131 |
| 7,015,935 B2 * | 3/2006 | Herget et al. | 345/649 |
| 7,215,325 B2 * | 5/2007 | Kim | 345/158 |
| 2002/0015006 A1 * | 2/2002 | Suzuki et al. | 345/6 |

FOREIGN PATENT DOCUMENTS

| | | |
|---|---|---|
| JP | 7-334702 | 12/1995 |
| JP | 2002-11000 | 1/2002 |

* cited by examiner (A)

SECTIONAL PLANE INCLINED ABOUT INTERSECTION OF SECTIONAL PLANE AND REFERENCE PLANE (INCLINATION IS RECORDED)

(B)

(C)

MOVED PARALLEL TOWARD POSITION OF PRESUMABLE CANINE AXIS (MOVEMENT AMOUNT IS RECORDED)

(A)

(B)

(C)

(D)

(E)

MEDICAL IMAGE PROCESSING DEVICE METHOD AND PROGRAM FOR DISPLAYING A SECTION FOR A CLINICAL APPLICATION

TECHNICAL FIELD

The present invention relates to a medical image processing apparatus and a medical image processing program. Particularly, the invention relates to an image processing apparatus and method, and an image processing program for constructing a three-dimensional image from multiple tomographic images picked up by CT, MRI or the like and forming a sectional image taken along any desired plane in the three-dimensional image.

PRIOR ART

With recent development of computer technology, there is known a technique for constructing a three-dimensional image from multiple tomographic images picked up by CT, MRI or the like. It is also possible to form a sectional image taken along any desired plane in the constructed three-dimensional image. For example, a medical image processing system is known, which is capable of forming a section having any desired orientation in a three-dimensional image by utilizing a so-called "oblique" function.

The section forming function of the conventional medical image processing system is capable of performing the following operations:
(1) To form any desired section in the three-dimensional image; and
(2) To form a section taken perpendicularly to any desired section defined as a reference plane.

However, the section formed by the conventional medical image processing system has the following drawbacks:
(1) Since the formation of the reference plane and the section is not based on anatomical characteristic points (landmarks), a correlation between a displayed image and a subject (patient) is inaccurate in clinical applications. Therefore, the section cannot efficiently be utilized for imaging diagnosis.
(2) Although the section perpendicular to the section defined as the reference plane can be formed, it is impossible to form a section intersecting the reference plane at a desired angle other than the right angle.

DISCLOSURE OF THE INVENTION

To overcome the aforesaid drawbacks, it is an object of the present invention to provide an image processing apparatus and method, and an image processing program, which are capable of displaying a section required for a clinical application in a medical imaging process.

It is another object of the present invention to provide a medical image processing apparatus and method, and a medical image processing program, which are capable of displaying a section in an accurately reproducible manner on the basis of anatomical characteristic points (landmarks).

It is further another object of the present invention to provide an image processing apparatus and method, and an image processing program, which can efficiently be utilized for clinical imaging diagnosis.

According to a first aspect of the invention, there is provided a medical image processing apparatus, which comprises: a display device for displaying an image; means which displays a three-dimensional medical image on the display device; means which specifies at least three points in the displayed three-dimensional image to define a reference plane passing through the three points in the three-dimensional image; first display switching means which switches the image displayed on the display device to a three-dimensional image viewed in a view direction perpendicular to the reference plane; second display switching means which, in response to definition of a sectional line in the three-dimensional image viewed in the view direction perpendicular to the reference plane, switches the image displayed on the display device to a three-dimensional image viewed in a view direction along the sectional line, and displays a line indicative of the reference plane and a line indicative of a sectional plane based on the sectional line together with this three-dimensional image; adjustment means which inclines the line indicative of the sectional plane displayed together with the three-dimensional image viewed in the view direction along the sectional line with respect to the line indicative of the reference plane; and means which displays an image taken along the sectional plane defined by the inclined line.

According to a second aspect of the invention, the medical image processing apparatus according to the first aspect of the invention is characterized in that the at least three points specified in the three-dimensional image are points specified by landmarks indicative of anatomical characteristic points, or markers.

According to a third aspect of the invention, the medical image processing apparatus according to the first or second aspects of the invention is characterized in that the adjustment means is further capable of moving the line indicative of the sectional plane along the line indicative of the reference plane.

According to a fourth aspect of the invention, there is provided a medical image processing method, which comprises the steps of: displaying a three-dimensional medical image; specifying at least three points in the displayed three-dimensional image to define a reference plane passing through the three points in the three-dimensional image; switching the displayed image to a three-dimensional image viewed in a view direction perpendicular to the reference plane; recognizing that a sectional line is defined in the three-dimensional image viewed in the view direction perpendicular to the reference plane; switching the displayed image to a three-dimensional image parallel to the reference plane and viewed in a view direction along the defined sectional line, and displaying a line indicative of the reference plane and a line indicative of a sectional plane based on the sectional line together with this three-dimensional image; inclining the line indicative of the sectional plane displayed together with the three-dimensional image viewed in the view direction along the sectional line with respect to the line indicative of the reference plane; and displaying an image taken along the sectional plane defined by the inclined line.

According to a fifth aspect of the invention, the medical image processing method according to the fourth aspect of the invention is characterized in that the at least three points specified in the displayed three-dimensional image are points specified by landmarks indicative of anatomical characteristic points, or markers contained in the three-dimensional image.

According to a sixth aspect of the invention, there is provided a medical image processing program, which comprises processes for: displaying a three-dimensional medical image viewed in a view direction perpendicular to a reference plane; defining a sectional line in the displayed three-dimensional medical image; displaying an image parallel to the reference plane and viewed along the defined sectional line together with a line indicative of the reference plane and a line indicative of a sectional plane based on the sectional line; recognizing that the line indicative of the sectional plane is adjusted with respect to the line indicative of the reference plane; and displaying a sectional image taken along the sectional plane defined by the line indicative of the adjusted sectional plane.

According to a seventh aspect of the invention, the medical image processing program according to the sixth aspect of the invention further comprises a process for specifying at least three points in the displayed three-dimensional medical image to define a plane passing through the three points as the reference plane in the displayed three-dimensional medical image.

According to the present invention, the formation of the section, which is conventionally achieved on a visual and sensory basis, can be realized as a process for displaying the section on the basis of the reference plane in a highly reproducible manner. Further, it is possible to define the sectional plane inclined with respect to the reference plane.

EMBODIMENTS OF THE INVENTION

With reference to the attached drawings, specific embodiments of the present invention will hereinafter be described by taking a dental application for example.

Where a dental implant is implanted in a canine deficient site of an upper jaw, for example, it is necessary to define the axis of a canine in a presumable implantation site with reference to the axes of neighboring teeth, and implant the dental implant along the defined axis.

To this end, a sectional image of the jaw taken in a presumable implantation direction along the axis of the canine is formed for use in diagnosis. If the sectional image of the jaw is oriented differently with respect to the axis of the canine, the image represents an inside portion of the jaw different from the presumable implantation site. Therefore, it is impossible to properly diagnose and determine the inside state of the jaw in the presumable implantation site, the length, size and shape of the dental implant required for the implantation.

Figure 1:
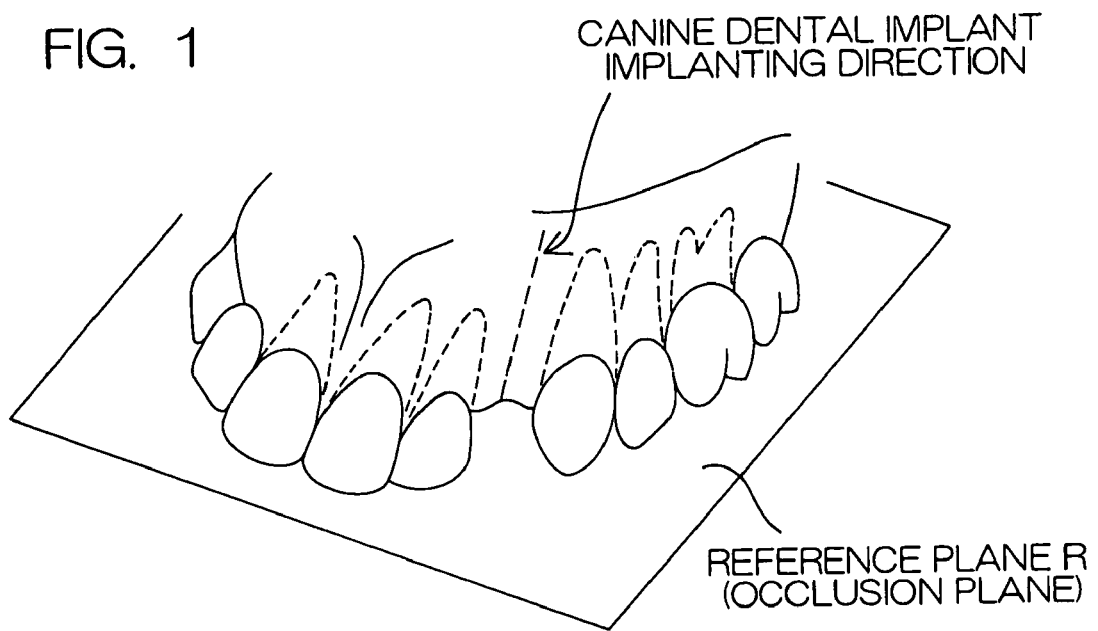
FIG. 1 is a schematic diagram illustrating a three-dimensional image of an upper jaw and an upper dental arch of a craniofacial portion.
Figure 2:
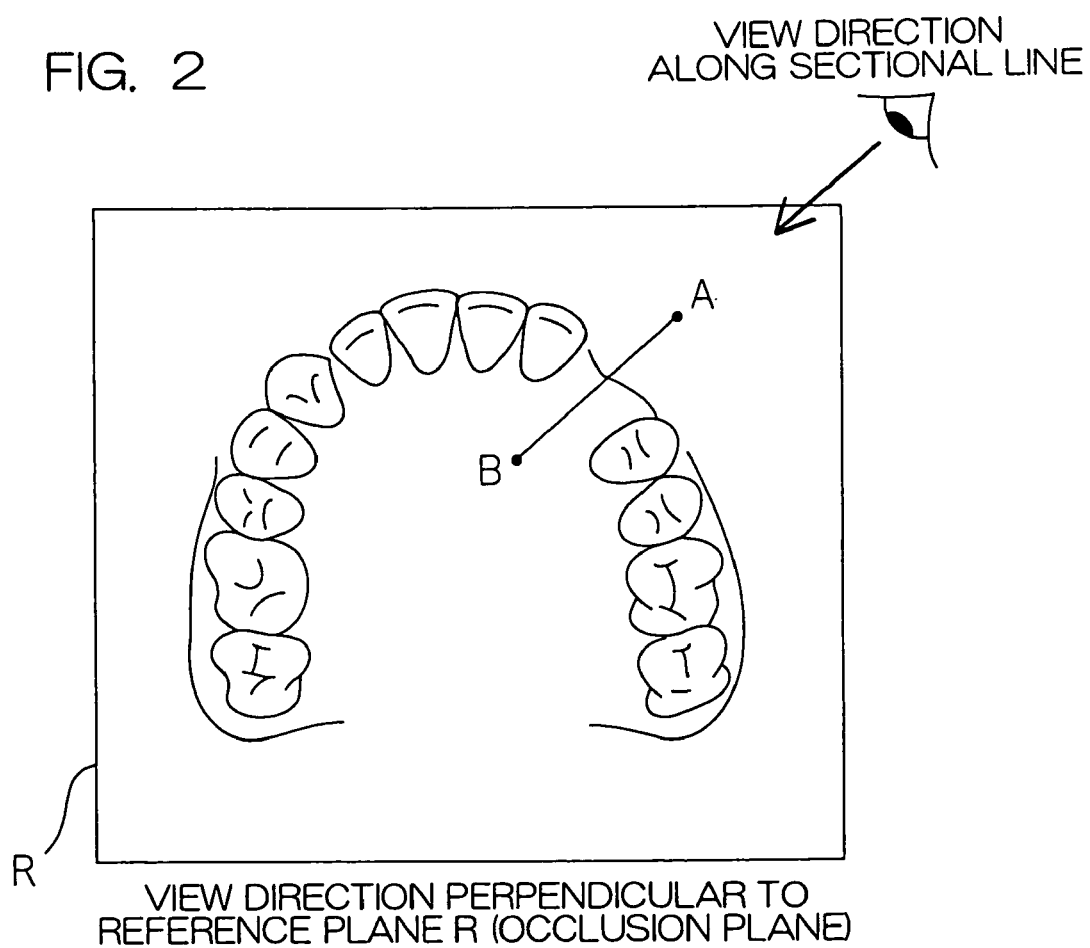
FIG. 2 is a schematic diagram illustrating a three-dimensional image viewed in a view direction perpendicular to a reference plane (occlusion plane) from a lower side of the reference plane.
Figure 3:
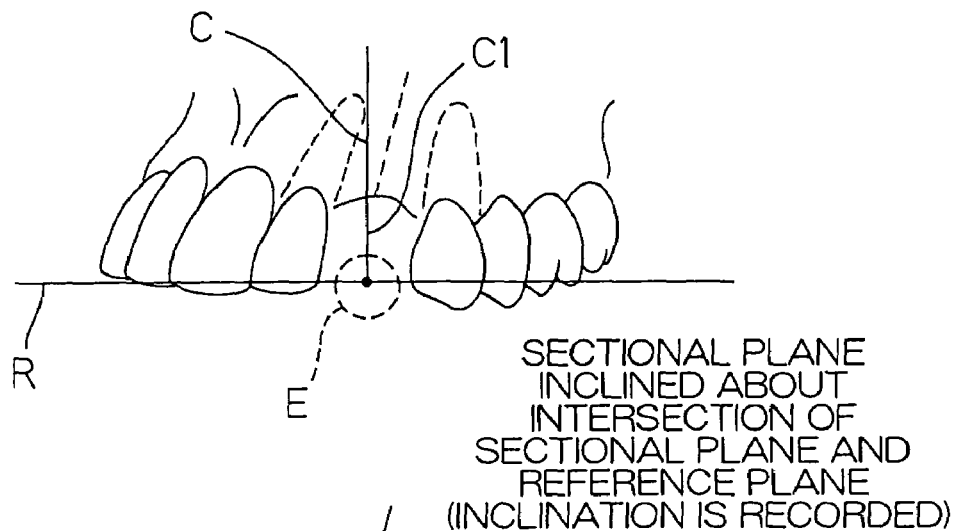
FIG. 3 are three-dimensional images such that the image shown in FIG. 2 is viewed laterally along a sectional line C.
Figure 3:
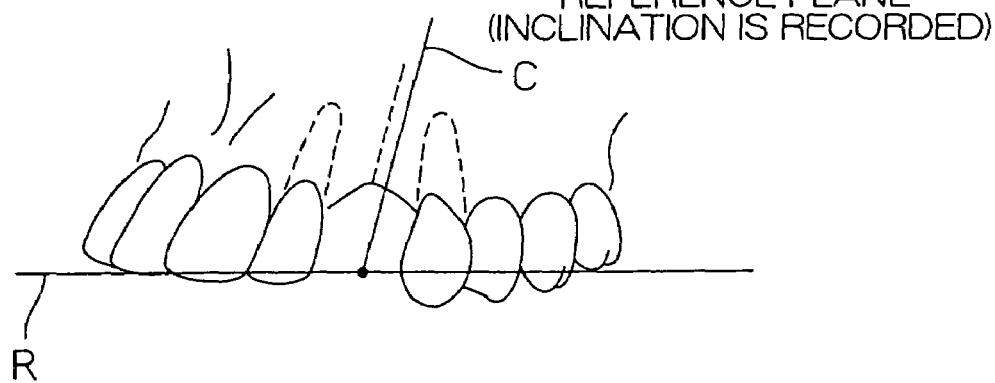
Figure 3:
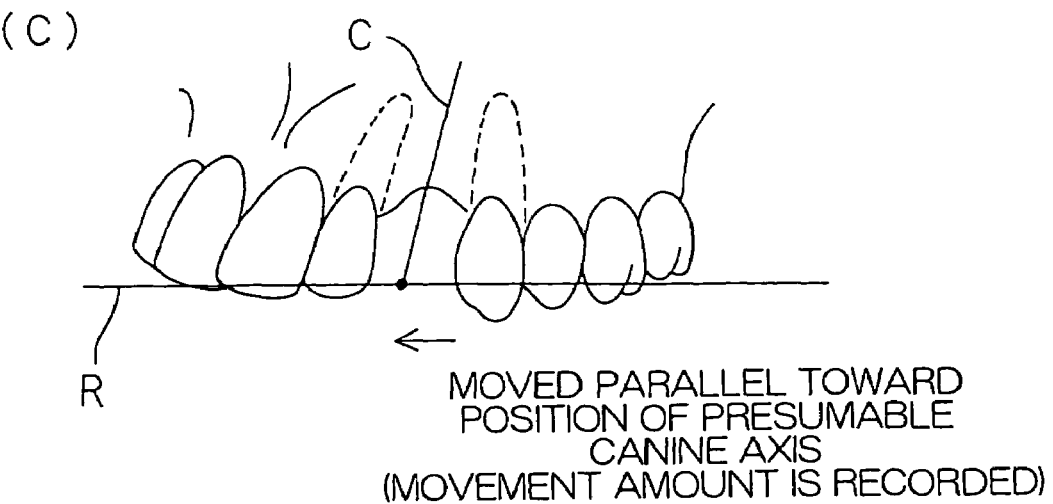

In this embodiment, images as shown in FIGS. 1 to 3 are displayed on a display device, and a sectional plane usable for clinical imaging diagnosis is provided.

FIG. 1 illustrates a three-dimensional image of an upper jaw and an upper dental arch of a cranio facial portion. This three-dimensional image is constructed from multiple tomographic images of a head of a patient picked up by CT, MRI or the like.

An occlusion plane is specified in the three-dimensional image of the upper jaw and the upper dental arch.

The specified occlusion plane is recognized as a reference plane R by a computer, and a three-dimensional image viewed perpendicularly to the reference plane R is displayed on the display device. That is, an image viewed in a view direction perpendicular to the reference plane R from a lower side of the reference plane R (occlusion plane) as shown in FIG. 2 is displayed.

A dentist or the like (hereinafter referred to as "user") defines a sectional line in the image of FIG. 2. The definition of the sectional line is achieved by inputting a start point A and an end point B. The defined sectional line is displayed together with the image.

Then, three-dimensional images are displayed such that the image shown in FIG. 2 is laterally viewed. These are shown in FIGS. 3A, 3B and 3C.

The three-dimensional image of FIG. 3A, which shows the upper jaw and the upper dental arch viewed along the reference plane (occlusion plane), is displayed together with the reference plane R and a sectional plane C perpendicular to the reference plane R (based on the sectional line defined in FIG. 2).

As shown in FIG. 3A, the sectional plane C is usually perpendicular to the reference plane R.

A feature of this embodiment is that the sectional plane C can be inclined with respect to the reference plane R as shown in FIG. 3B. That is, the sectional plane C can be inclined about an intersection of the reference plane R and the sectional plane C as shown in FIG. 3B. By inclining the sectional plane C, the sectional plane C can be adjusted at an angle of the axis of the canine. This process can be performed by dragging an upper portion of the sectional plane C rightward.

Further, the sectional plane C can be moved parallel along the reference plane R as shown in FIG. 3C. The movement can be achieved by dragging the intersection E of the sectional plane C and the reference plane R leftward. The inclination angle of the sectional plane C is not changed by the movement of the sectional plane C. The movement of the sectional plane C makes it possible to align the sectional plane C with a presumable canine axis.

Then, the resulting sectional plane C is displayed. The sectional plane C provides a section of the canine deficient site (the presumable implantation site for the dental implant) in the jaw.

Figure 4:
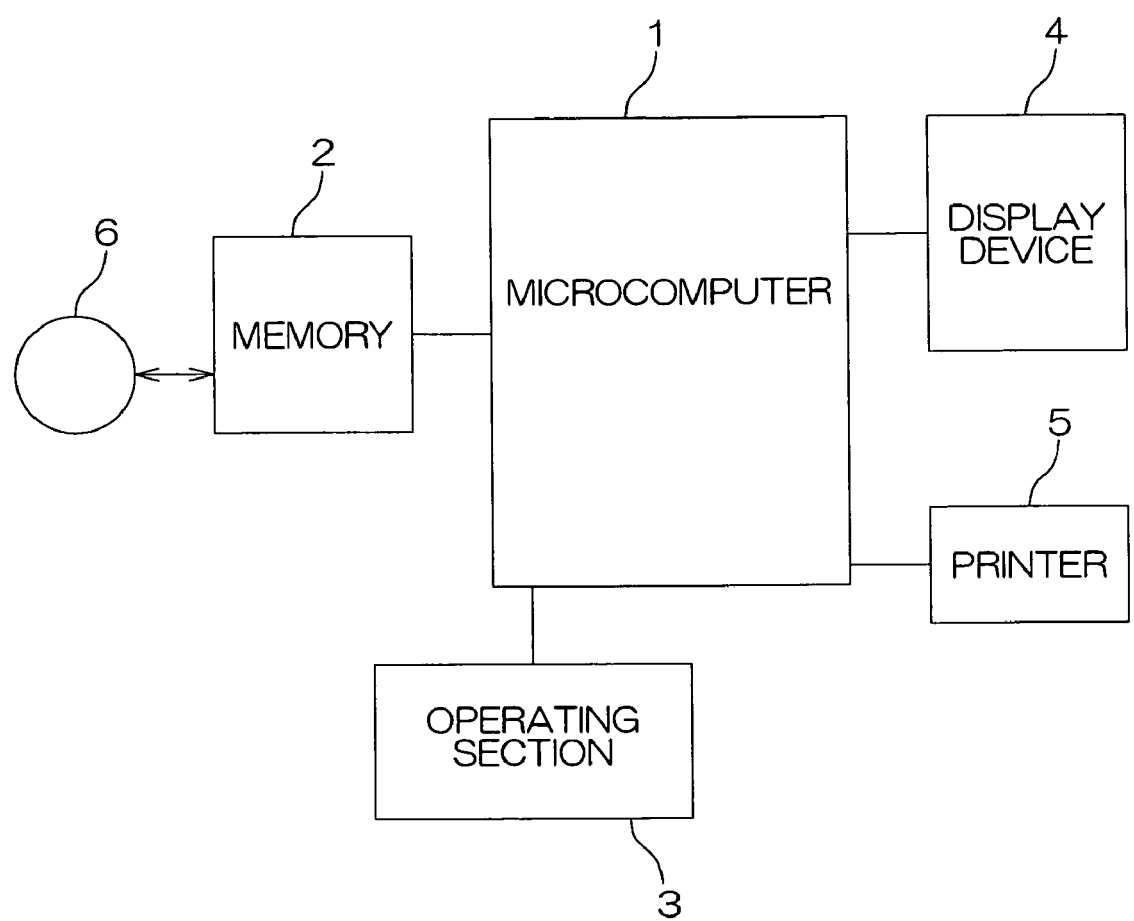
FIG. 4 is a block diagram illustrating the schematic construction of a medical image processing apparatus according to one embodiment of the present invention.

FIG. 4 is a block diagram illustrating the schematic construction of a medical image processing apparatus according to one embodiment of the present invention. The apparatus includes a microcomputer 1 as a central unit. The microcomputer 1 is connected to a memory 2, an operating section 3, a display device 4 and a printer 5. The memory 2 may include a RAM, a ROM, a hard disk and the like. The memory 2 may be mounted with a removable disk-shaped memory medium 6. The operating section 3 includes a keyboard, a touch panel input device and the like for inputting data and commands. The operating section 3 may include a muse.

The display device 4 is adapted to display image data characteristic of the present invention. The printer 5 is adapted to print out the image data displayed on the display device 4 as required.

Figure 5:
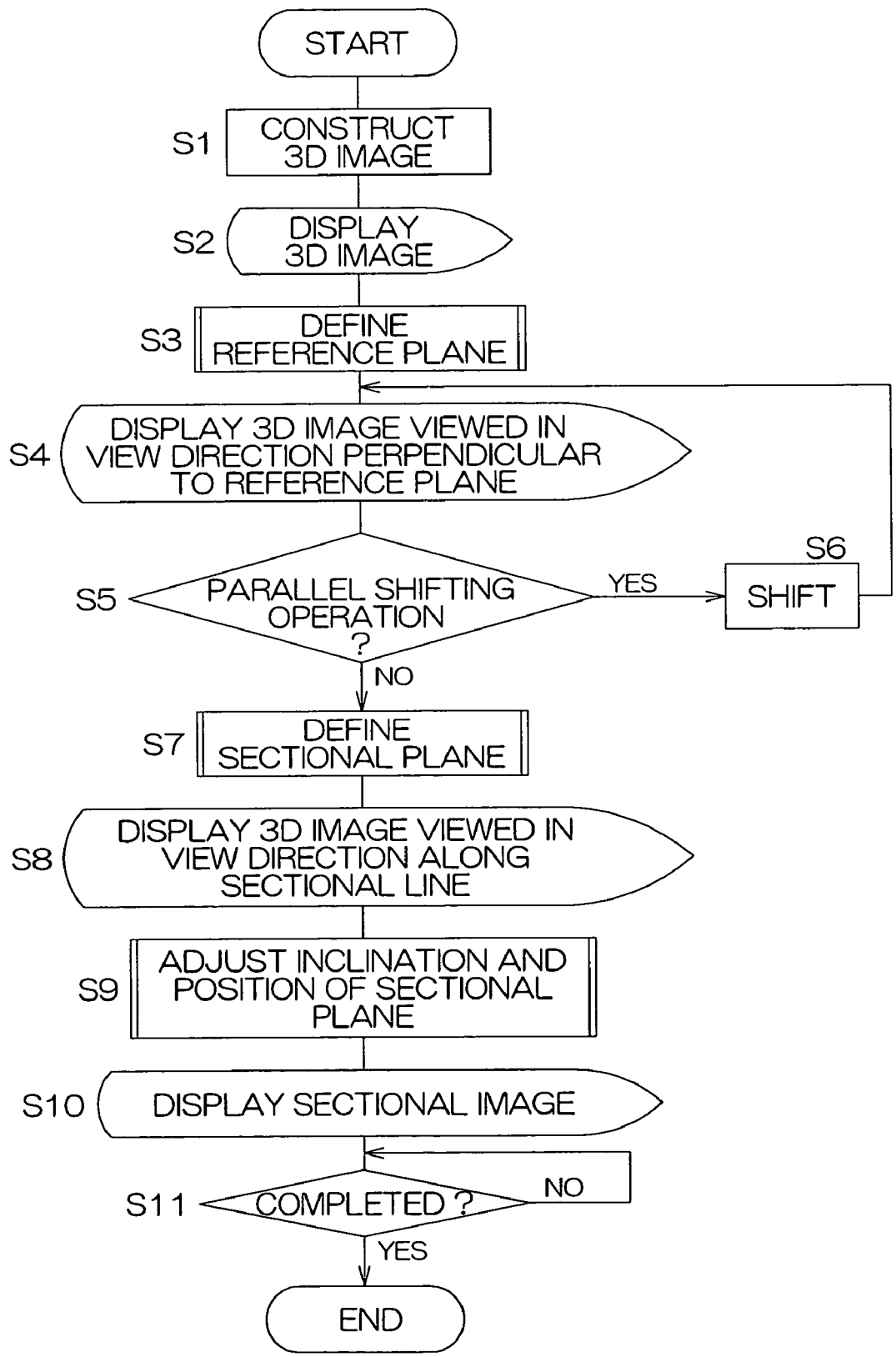
FIG. 5 is a flow chart illustrating an image processing operation to be performed by a microcomputer.

FIG. 5 is a flow chart illustrating an image processing operation to be performed by the microcomputer 1 shown in FIG. 4.

An explanation will be given in accordance with the flow chart of FIG. 5. First, the microcomputer 1 constructs a three-dimensional image (Step S1). The construction of the three-dimensional image is based on multiple tomographic image data stored in the memory 2 or the like. The constructed three-dimensional image is displayed on the display device 4 (Step S2). The three-dimensional image displayed on the display device 4 can be moved or rotated so as to be viewed in different view directions as required. A reference plane is defined by operating the operating section 3 while viewing the three-dimensional image (Step S3). Upon the definition of the reference plane, the defined reference plane R (e.g., occlusion plane) is displayed together with the three-dimensional image as shown in FIG. 1.

After the definition of the reference plane, the microcomputer 1 switches the image displayed on the display device 4 to a three-dimensional image viewed in a view direction perpendicular to the reference plane (Step S4). This image is as shown in FIG. 2. The three-dimensional image viewed in the view direction perpendicular to the reference plane can be shifted to provide a sectional image parallel to the reference plane by operating the operating section 3 (Steps S5→S6→S4).

Figure 6:
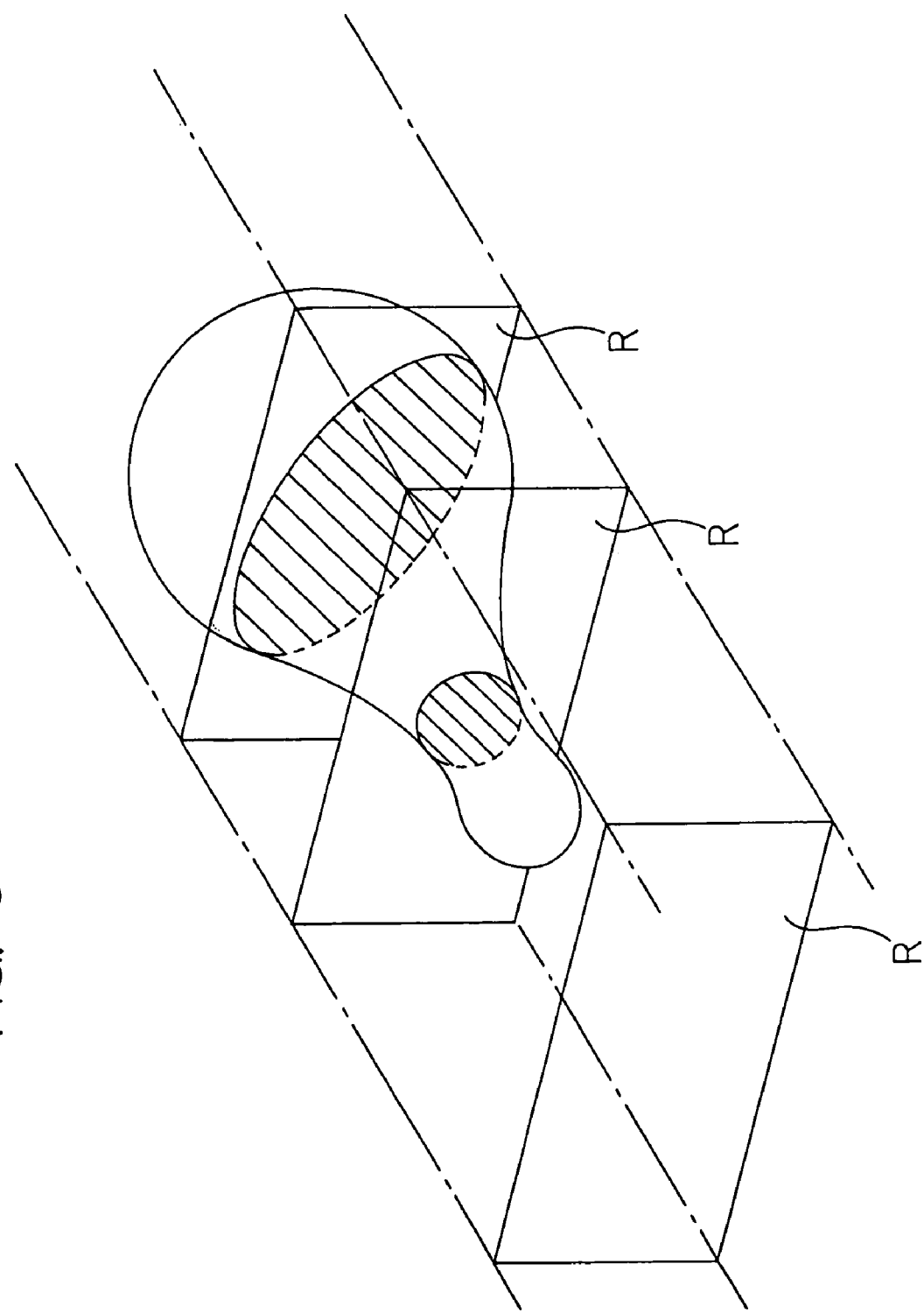
FIG. 6 is a diagram for explaining how to switch a displayed three-dimensional image.

That is, the three-dimensional image displayed on the display device 4 can be switched to a three-dimensional image viewed from the outside of the object or to a sectional image at any desired depth of the object as schematically illustrated in FIG. 6.

A sectional line defining process is performed on the image (the three-dimensional image or the sectional image) displayed as viewed in the view direction perpendicular to the reference plane on the display device 4 (Step S7). This process is performed as explained with reference to FIG. 2, and will be described later in greater detail.

After the sectional line defining process, the microcomputer 1 switches the image displayed on the display device 4 to a three-dimensional image viewed in a view direction along the sectional line (Step S8). This image is as shown in FIG. 3A. A sectional plane (expressed by a line) based on the sectional line defined in the Step S7 is displayed together with the reference plane (also expressed by a line) in the three-dimensional image viewed in the view direction along the sectional line.

Next, the inclination adjustment of the sectional plane and the positional adjustment of the sectional plane are performed by operating the operating section 3 while viewing the three-dimensional image displayed as viewed in the view direction along the sectional line on the display device 4 (Step S9).

After these adjustments are performed, the resulting sectional image is displayed on the display device 4 (Step S10).

By inputting a completion command (Step S11), the process ends.

Figure 7:
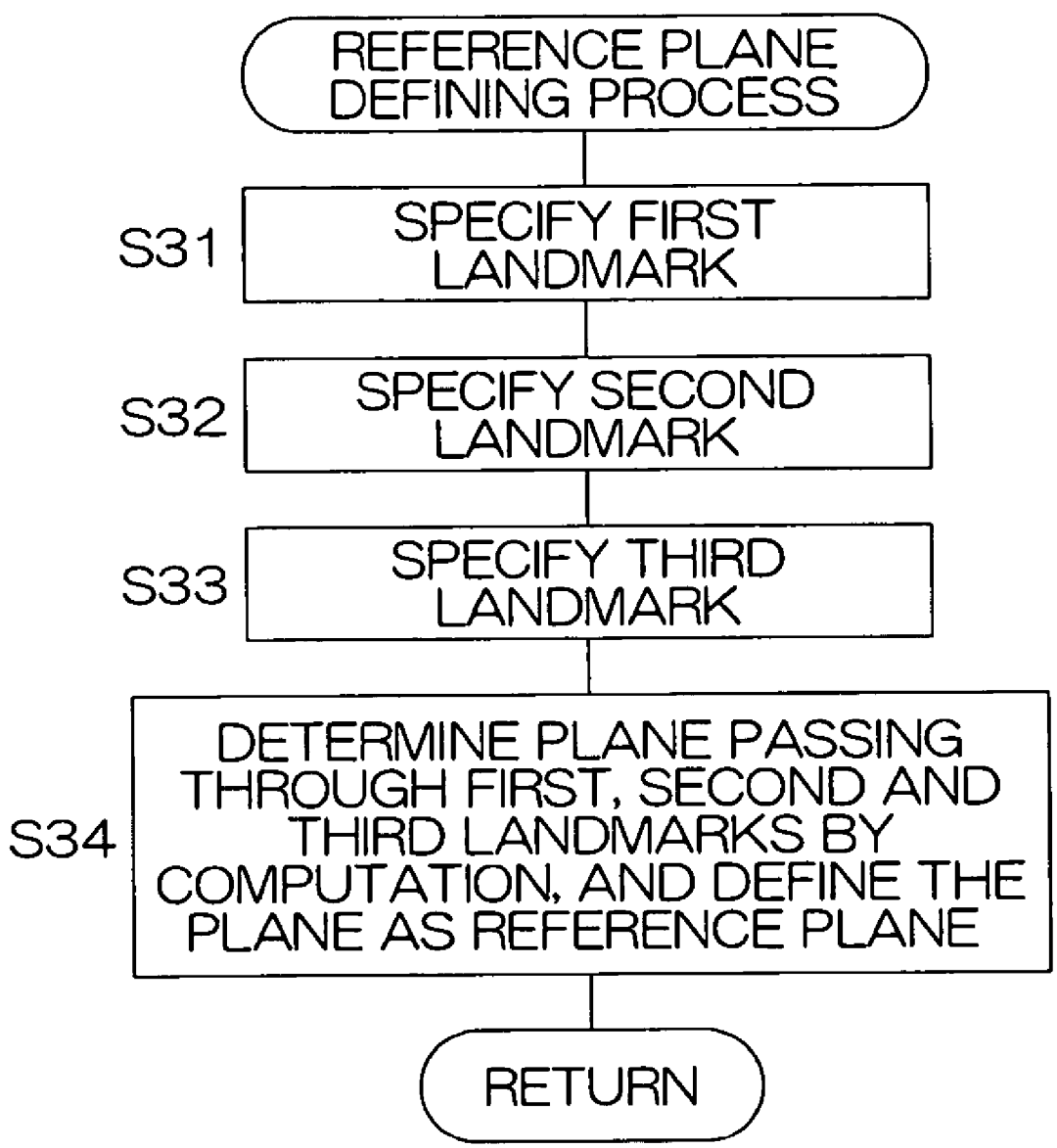
FIG. 7 is a flow chart illustrating a reference plane defining process in detail.

FIG. 7 is a flow chart illustrating the reference plane defining process in Step S3 of FIG. 5 in detail. In the reference plane defining process, a first landmark is first specified (Step S31). Then, a second landmark is specified (Step S32). Further, a third landmark is specified (Step S33).

The specification of these three landmarks is achieved by operating the operating section 3 to specify any anatomical reference points in the three-dimensional image displayed on the display device 4. Where the occlusion plane is defined in the three-dimensional image of the upper jaw and the upper dental arch shown in FIG. 1, for example, the center of a buccal face of a left first molar, the center of a buccal face of a right first molar and the center of a left lateral incisor are specified as the first landmark, the second landmark and the third landmark, respectively. The center of the right lateral incisor or the middle between the left and right lateral incisors may be specified as the third landmark.

Upon the specification of the three landmarks (Steps S31 to S33), the microcomputer 1 determines a plane passing through the three specified landmarks by computation, and stores the plane as the reference plane (Step S34).

Since the reference plane is thus defined by the three landmarks, i.e., by the anatomical characteristic points, the reference plane passing through the three landmarks is a clinically significant and reproducible reference plane. There are various landmarks on human bones. Therefore, it is preferred to utilize any of these landmarks in the case of an image containing a bone. Besides the landmarks, markers may be utilized. Where a three-dimensional image is constructed on the basis of multiple tomographic images obtained by CT or the like with the markers applied on a patient, the markers are contained in the image. A plane passing through display positions of the markers may be defined as the reference plane.

Figure 8:
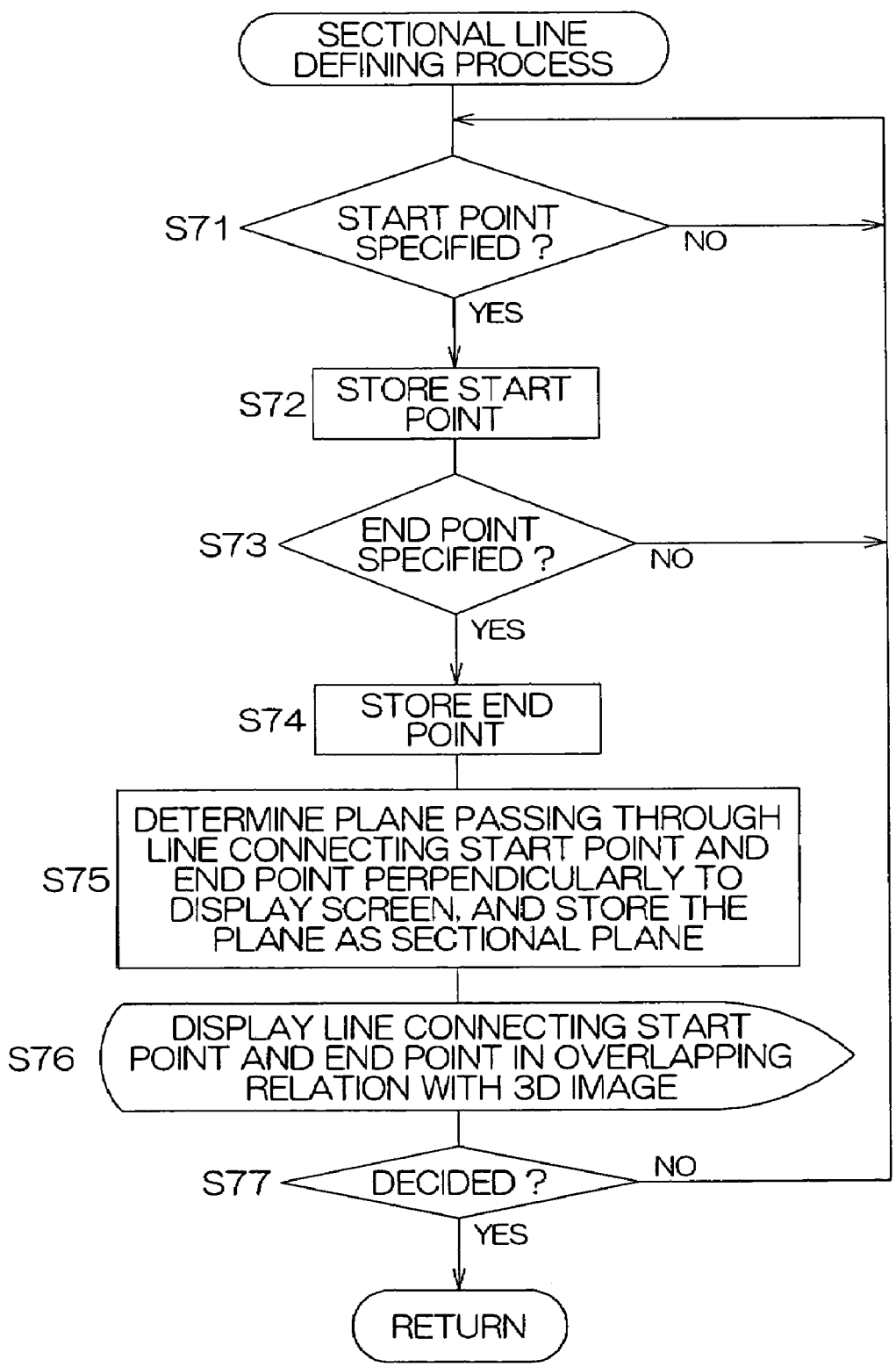
FIG. 8 is a flow chart illustrating a sectional plane defining process in detail.

FIG. 8 is a flow chart illustrating the sectional line defining process in Step S7 of FIG. 5 in detail. In the sectional line defining process, the operating section 3 is operated to specify a start point (Step S71). That is, a point A is specified in the image of FIG. 2 displayed on the display device 4, for example, by the mouse. Then, the position of the start point A is stored (Step S72). Further, the mouse is moved to a position different from the position of the start point A and, for example, a position B is clicked by the mouse for specifying an end point B (Step S73). Then, the coordinates of the end point B is stored in the microcomputer 1 (Step S74).

In turn, the microcomputer 1 determines a sectional plane passing through a line connecting the start point A and the end point B perpendicularly to a screen of the display device 4, i.e., perpendicularly to the image of FIG. 2, by computation, and stores the sectional plane (Step S75).

Then, the line connecting the start point A and the end point B is displayed in overlapping relation with the three-dimensional image (Step S76). The display is as shown in FIG. 2.

When a decision command is inputted from the operating section 3, e.g., a decision key is pressed, in view of this display (Y in Step S77), the process is returned.

Figure 9:
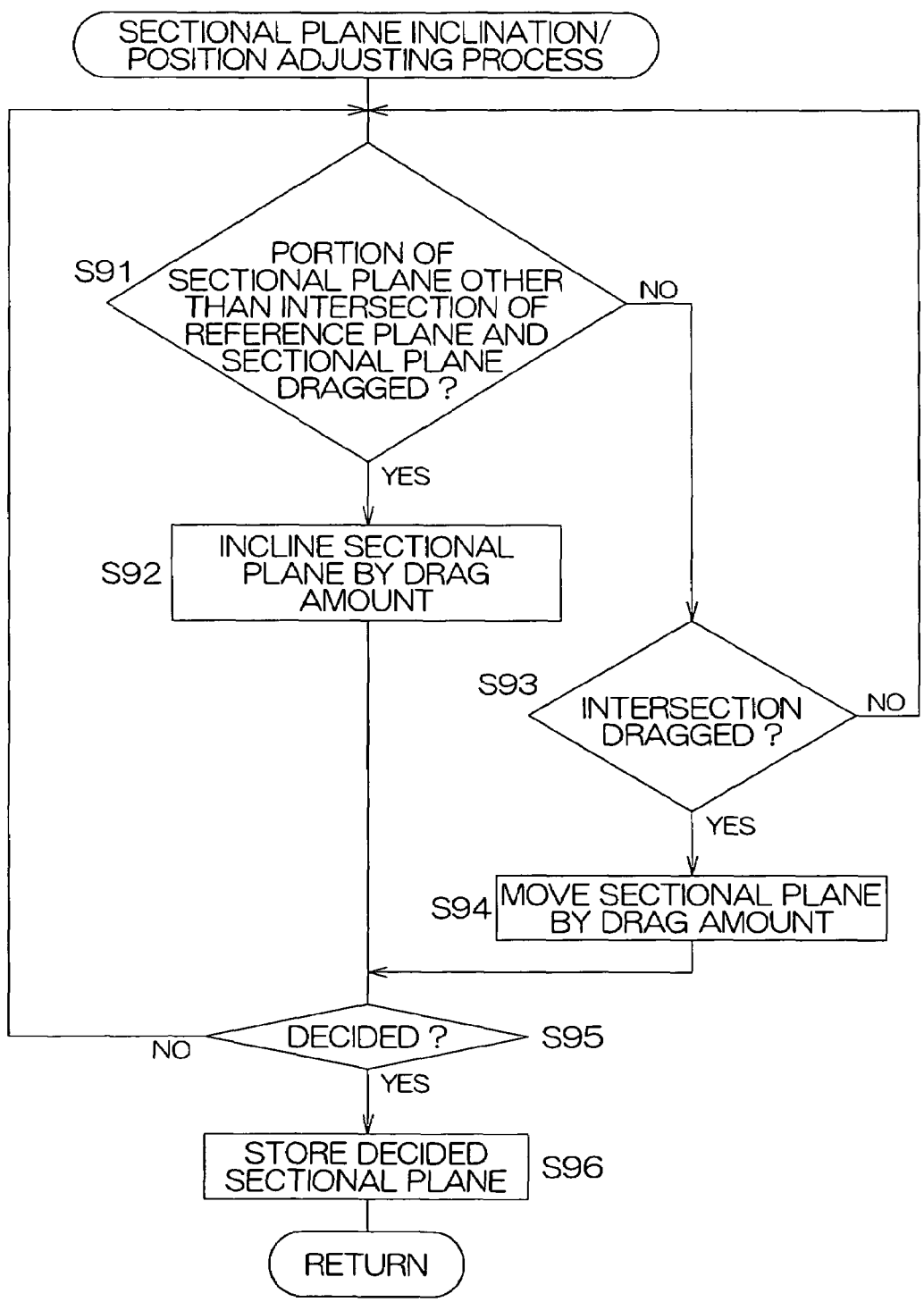
FIG. 9 is a flow chart illustrating a sectional plane inclination and position adjusting process.

FIG. 9 is a flow chart illustrating the sectional plane inclination/position adjusting process in Step S9 of FIG. 5 in detail.

In the sectional plane inclination/position adjusting process, the image shown in FIG. 3A is displayed on the display device 4 in Step S8 of FIG. 5. That is, the three-dimensional image viewed in the view direction along the sectional line C (see FIG. 2), the reference plane R (expressed by a line) overlapped with the three-dimensional image and the sectional plane C (also expressed by a line) are displayed.

In view of the display on the display device 4, the operating section 3 is operated. For example, a portion C1 of the sectional plane C is pointed and dragged, for example, by the mouse. Then, the line indicative of the sectional plane C is inclined about an intersection of the sectional plane C and the reference plane R at an inclination angle corresponding to a drag amount (see FIG. 3B). That is, the sectional plane C can be inclined about the intersection of the sectional plane C and the reference plane R (Step S92).

Further, the intersection of the sectional plane C and the reference plane R is pointed and dragged along the reference plane R, whereby the sectional plane C is moved parallel by a drag amount (Steps S93, S94).

Through the aforesaid process, the sectional plane C can be adjusted at a desired inclination angle at a desired position with respect to the reference plane R. By pressing the decision key, the decided sectional plane is stored in the microcomputer 1 (Steps S95, S96). Then, the process is returned.

Although the process described above is such that the inclination angle and position of the sectional plane C are adjusted with respect to the reference plane R, the process may be such that, after the adjustment of the inclination angle and position of the sectional plane C, the reference plane R is rotated and moved so as to be set perpendicular to the sectional plane C, and then stored. With this arrangement, where the reference plane cannot be defined in a proper orientation in a proper region due to difficulty in specifying the landmarks, a new reference plane may be defined on the basis of a sectional plane, which is defined on the basis of another reference plane. Thus, the sectional plane is defined on the basis of the original reference plane, and then the new reference plane is defined on the basis of this sectional plane. Therefore, the positional relationship among the respective planes can uniquely be determined on the basis of the original reference plane. Therefore, continuous sectional images can be formed without deteriorating the reproducibility of the sectional images.

The coordinates of the landmarks used for the definition of the reference plane, the coordinates of the inputted points required for the definition of the sectional plane, the inclination and the parallel movement amount, which are all stored in the microcomputer 1, can numerically be encoded and displayed as required. The numerical display is useful for the user to recognize the positional relationship between the sectional plane and the reference plane. Therefore, the apparatus has an improved operability.

In the foregoing explanation, the sectional line C is defined in the image viewed in the view direction perpendicular to the reference plane (see Step S7 of FIG. 5). Alternatively, the sectional line C may be defined as having a thickness (or a width) for extracting a three-dimensional image (information) within the sectional region having the thickness in the present invention.

Figure 10:
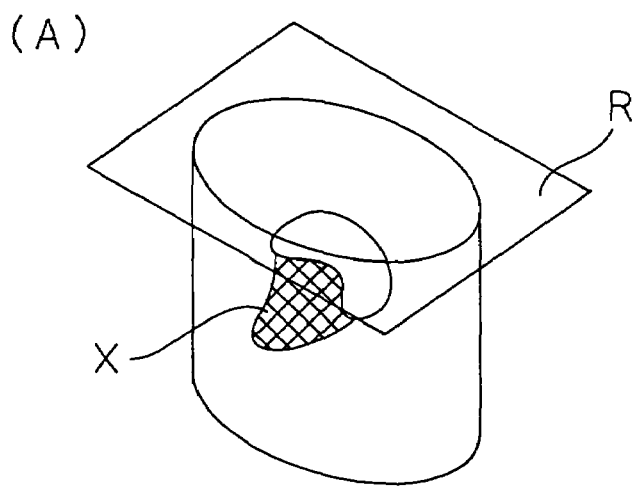
FIG. 10 are diagrams for explaining a process for defining a minimum extraction region embracing a region X of interest.
Figure 10:
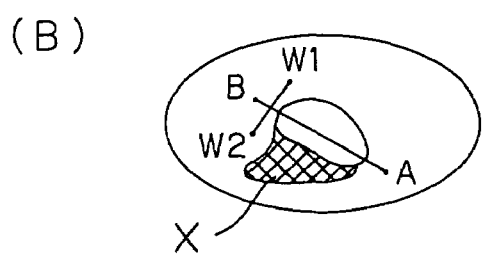
Figure 10:
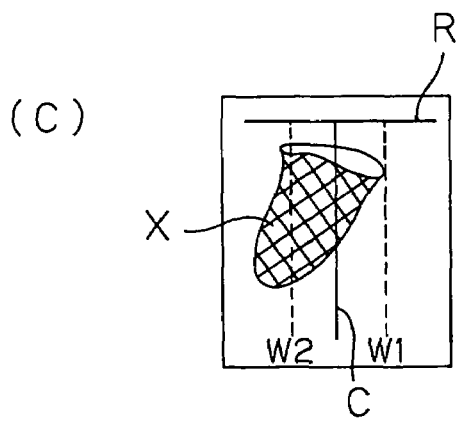
Figure 10:
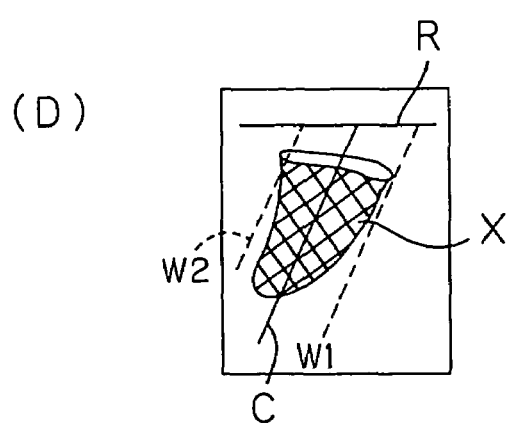
Figure 10:
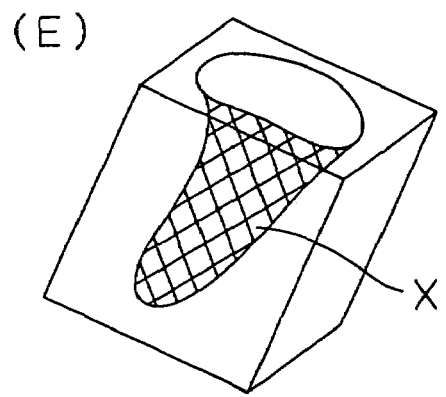

More specifically, a reference plane R is first defined in a three-dimensional image as shown in FIG. 10A.

Then, an image viewed in a view direction perpendicular to the reference plane R is displayed. This image is as shown in FIG. 10B. A sectional line A-B and a thickness W1-W2 as measured perpendicularly to the sectional line A-B are defined in this image.

Subsequently, an image viewed in a view direction along the sectional line A-B is displayed. This image is as shown in FIG. 10C. In FIG. 10C, there are shown the reference plane R, the sectional plane C, and the widths W1, W2 as measured from the sectional plane C. The line C indicative of the sectional plane C may be defined as having a predetermined length from an intersection of the sectional plane C and the reference plane R. Thus, an extraction region to be described later can more specifically be defined within a desired range.

Then, the inclination of the sectional plane C with respect to the reference plane R is adjusted on the display as shown in FIG. 10D and, as required, the sectional plane C is moved parallel along the reference plane R. Thus, the lines W1, W2 defining the width of the sectional plane C are automatically moved.

Then, a sectional region defined centrally along the sectional plane C by the width W1-W2 is extracted as shown in FIG. 10E.

Thus, it is possible to define a minimum extraction region as embracing a region X of interest, and extract the region X as three-dimensional image information.

Although the implantation of the dental implant in the canine deficient site of the jaw has been explained in the aforesaid embodiment, the present invention is applicable to a case where sectional images along the axes of all teeth arranged in the upper dental arch are displayed on the basis of the occlusion plane. In this case, the respective teeth of the upper dental arch have different inclination angles with respect to the occlusion plane. Therefore, the inclination angles of the teeth are preliminarily determined so that the sectional images along the axes of the respective teeth can automatically be displayed. That is, where continuous sections in a wide range are to be formed on the basis of the same reference plane, it is possible to set inclination conditions for a plurality of regions and successively form the sections at the inclination angles defined for the respective regions. Such a function can automatically be realized by preliminarily defining an average inclination angle.

The present invention is not limited to the image processing apparatus and the processing program for the apparatus in the dental field. For example, the present invention is applicable to a case where it is desired to display a three-dimensional image of a human organ such as stomach and display an image taken along a sectional plane defined on the basis of any desired sectional plane defined as a reference plane. Thus, the present invention is applicable to image processing apparatuses and processing programs for the apparatuses in various medical fields.

What is claimed is:

1. A medical image processing apparatus comprising:
   a display device for displaying an image;
   means which displays a three-dimensional medical image on the display device;
   means which specifies at least three points in the displayed three-dimensional image to define a reference plane passing through the three points in the three-dimensional image;
   first display switching means which switches the image displayed on the display device to a three-dimensional image viewed in a view direction perpendicular to the reference plane;
   second display switching means which, in response to definition of a sectional line in the three-dimensional image viewed in the view direction perpendicular to the reference plane, switches the image displayed on the display device to a three-dimensional image viewed in a view direction along the sectional line, and displays a line indicative of the reference plane and a line indicative of a sectional plane based on the sectional line together with this three-dimensional image;
   adjustment means which inclines the line indicative of the sectional plane displayed together with the three-dimensional image viewed in the view direction along the sectional line independently with respect to the line indicative of the reference plane, wherein the adjustment means is further capable of moving the inclined line indicative of the sectional plane independently along the line indicative of the reference plane in parallel thereto, and wherein the adjustment means maintains the line indicative of the reference plane at the original position; and means which displays an image taken along the sectional plane defined by the inclined line.

2. A medical image processing apparatus as set forth in claim 1, wherein the at least three points specified in the three-dimensional image are points specified by landmarks indicative of anatomical characteristic points, or markers.

3. A medical image processing method comprising the steps of:
displaying a three-dimensional medical image;
specifying at least three points in the displayed three-dimensional image to define a reference plane passing through the three points in the three-dimensional image;
switching the displayed image to a three-dimensional image viewed in a view direction perpendicular to the reference plane;
recognizing that a sectional line is defined in the three-dimensional image viewed in the view direction perpendicular to the reference plane;
switching the displayed image to a three-dimensional image parallel to the reference plane and viewed in a view direction along the defined sectional line, and displaying a line indicative of the reference plane and a line indicative of a sectional plane based on the sectional line together with this three-dimensional image;
inclining the line indicative of the sectional plane displayed together with the three-dimensional image viewed in the view direction along the sectional line independently with respect to the line indicative of the reference plane, moving the inclined line indicative of the sectional plane independently along the line indicative of the reference plane in parallel thereto, maintaining the line indicative of the reference plane at the original position; and
displaying an image taken along the sectional plane defined by the inclined line.

4. A medical image processing method as set forth in claim 3, wherein the at least three points specified in the displayed three-dimensional image are points specified by landmarks indicative of anatomical characteristic points, or markers contained in the three-dimensional image.

5. A computer program product for medical image processing, the computer program product comprising:
a computer readable medium having computer readable program code embodied therewith, the computer readable program code comprising:
instructions to display a three-dimensional medical image viewed in a view direction perpendicular to a reference plane;
instructions to define a sectional line in the displayed three-dimensional medical image;
instructions to display an image parallel to the reference plane and viewed along the defined sectional line together with a line indicative of the reference plane and a line indicative of a sectional plane based on the sectional line;
instructions to recognize that the line indicative of the sectional plane is adjusted independently with respect to the line indicative of the reference plane, and instructions to move the inclined line indicative of the sectional plane independently along the line indicative of the reference plane in parallel thereto, maintaining the line indicative of the reference plane at the original position; and
instructions to display a sectional image taken along the sectional plane defined by the line indicative of the adjusted sectional plane.

6. The computer program product as set forth in claim 5 further comprising instructions to specify at least three points in the displayed three-dimensional medical image to define a plane passing through the three points as the reference plane in the displayed three-dimensional medical image.

* * * * *